US008680125B2

(12) United States Patent
Kepley et al.

(10) Patent No.: US 8,680,125 B2
(45) Date of Patent: Mar. 25, 2014

(54) FULLERENE THERAPIES FOR INFLAMMATION

(75) Inventors: Christopher L. Kepley, Ringgold, VA (US); Robert P. Lenk, Danville, VA (US); Stephen R. Wilson, Danville, VA (US); Zhiguo Zhou, Winston-Salem, NC (US); Darren K. MacFarland, Danville, VA (US)

(73) Assignee: Luna Innovations Incorporated, Roanoke, VA (US)

( * ) Notice: Subject to any disclaimer, the term of this patent is extended or adjusted under 35 U.S.C. 154(b) by 341 days.

(21) Appl. No.: 12/921,049

(22) PCT Filed: Mar. 3, 2009

(86) PCT No.: PCT/US2009/001333
§ 371 (c)(1),
(2), (4) Date: Sep. 3, 2010

(87) PCT Pub. No.: WO2009/114088
PCT Pub. Date: Sep. 17, 2009

(65) Prior Publication Data
US 2011/0028522 A1 Feb. 3, 2011

Related U.S. Application Data

(60) Provisional application No. 61/033,309, filed on Mar. 3, 2008.

(51) Int. Cl.
*A61K 31/41* (2006.01)
*A61K 31/235* (2006.01)
*C07D 403/00* (2006.01)
*C07C 67/48* (2006.01)

(52) U.S. Cl.
USPC .................. 514/359; 514/532; 548/255

(58) Field of Classification Search
USPC ............... 560/81, 82; 548/255; 514/359, 532
See application file for complete search history.

(56) References Cited

U.S. PATENT DOCUMENTS

| 8,241,648 | B2 * | 8/2012 | Zhou et al. ............... 424/401 |
|---|---|---|---|
| 2003/0027870 | A1 | 2/2003 | Wilson et al. |
| 2008/0213324 | A1 | 9/2008 | Zhou et al. |
| 2011/0003773 | A1 | 1/2011 | Kepley et al. |
| 2011/0009486 | A1 | 1/2011 | Kepley et al. |
| 2011/0021630 | A1 | 1/2011 | Kepley et al. |
| 2011/0190251 | A1 | 8/2011 | Kepley et al. |

FOREIGN PATENT DOCUMENTS

| EP | 1 834 637 A1 | 9/2007 |
|---|---|---|
| EP | 1 867 337 A1 | 12/2007 |
| WO | 2005/035441 A2 | 4/2005 |
| WO | 2005/037711 A1 | 4/2005 |
| WO | 2006/077597 A2 | 7/2006 |

(Continued)

OTHER PUBLICATIONS

International Search Report (PCT/ISA/210) dated Oct. 13, 2009.

(Continued)

*Primary Examiner* — Shengjun Wang
(74) *Attorney, Agent, or Firm* — ATFirm PLLC; Susan M. Dadio

(57) ABSTRACT

Described herein are methods for treating inflammatory disorders. The methods comprise administering to a subject in need thereof a therapeutically effective amount of a synthetically modified fullerene.

3 Claims, 11 Drawing Sheets

(56) References Cited

FOREIGN PATENT DOCUMENTS

| WO | 2008/109032 A2 | 9/2008 |
|---|---|---|
| WO | 2009/114084 A2 | 9/2009 |
| WO | 2009/114087 A2 | 9/2009 |
| WO | 2009/114089 A2 | 9/2009 |
| WO | 2009/114090 A2 | 9/2009 |

OTHER PUBLICATIONS

Search report and written opinion issued on Nov. 16, 2012 for corresponding European application No. 09 718 906.2.

Martin Braun et al., "Amphiphilic [5:1]- and [3:3]-Hexakisadducts of C60," Eur. J. Org. Chem. (2004) pp. 1983-2001, Wiley-VCH Verlag GmbH & Co. KGaA, Weinheim, Germany.

Andreas Hirsch et al., "C60 Hexakisadducts with an Octahedral Addition Pattern 2 A New Structure Motif in Organic Chemistry," Eur. J. Org. Chem. (2001) pp. 829-848, Wiley-VCH Verlag GmbH & Co. KGaA, Weinheim, Germany.

Martin Braun et al., "Synthesis of a Biotinated Lipofullerene as a New Type of Transmembrane Anchor," Eur. J. Org. Chem. (2000) pp. 1173-1181, Wiley-VCH Verlag GmbH & Co. KGaA, Weinheim, Germany.

Patent Examination Report No. 1 issued on Aug. 1, 2013 for corresponding Australian Patent Application No. 2009223841.

* cited by examiner

FULLERENE THERAPIES FOR INFLAMMATION

BACKGROUND

Various embodiments described herein relate to the use of fullerenes to treat inflammatory disorders.

Inflammation is the complex biological response of tissues to harmful stimuli, such as pathogens, damaged cells, or irritants. However, inflammation which runs unchecked can lead to a host of disorders, such as inflammatory arthritis, rheumatoid arthritis, hay fever, and atherosclerosis.

Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Acute inflammation is a short-term process which is characterized by the classic signs of inflammation—swelling, redness, pain, heat, and loss of function—due to the infiltration of the tissues by plasma and leukocytes. It occurs as long as the injurious stimulus is present and ceases once the stimulus has been removed, broken down, or walled off by scarring (fibrosis).

Prolonged inflammation, known as chronic inflammation, leads to a progressive shift in the type of cells which are present at the site of inflammation and is characterized by simultaneous destruction and healing of the tissue from the inflammatory process. Chronic inflammation is a pathological condition characterized by concurrent active inflammation, tissue destruction, and attempts at repair. Chronic inflammation is not characterized by the classic signs of acute inflammation listed above. Instead, chronically inflamed tissue is characterized by the infiltration of mononuclear immune cells (monocytes, macrophages, lymphocytes, and plasma cells), tissue destruction, and attempts at healing, which include angiogenesis and fibrosis. Endogenous causes include persistent acute inflammation. Exogenous causes are varied and include bacterial infection, prolonged exposure to chemical agents such as silica, or autoimmune reactions such as rheumatoid arthritis.

Cells of the immune system use a signal cascade to mount an escalating response to a real or perceived insult. The inflammatory response becomes pathogenic when the signal cascade is invoked inappropriately. For example, autoimmune diseases are the consequence of the immune system mounting a response against antigens which are intrinsic. Many anti-inflammatory agents function by inhibiting the signal cascade, such as by blocking intracellular or intercellular effectors. Glucocorticoids, for example, mimic the natural immune suppressant, cortisol, to block genes at the transcription level, and cylco-oxygenase inhibitors are small molecules that bind to and inhibit enzymes that processes an internal signal molecule in cells.

Fullerene molecules are a family of carbon allotropes that comprise closed cages of generally 60 to 200 carbon atoms and may also include chemical moieties attached to the exterior or incorporated within the cage. Fullerenes can be in the form of a hollow sphere, ellipsoid, or tube. The most common fullerene to date is the $C_{60}$ Buckminsterfullerene (IUPAC name $(C_{60}\text{-Ih})[5,6]$fullerene). Another fairly common buckminsterfullerene is $C_{70}$, but fullerenes with 72, 76, 84 and even up to 100 carbon atoms are commonly obtained. Fullerene molecules can contain as few as 20 or more than 500 carbon atoms. Fullerenes may enclose one or more atoms such as metal atoms, or other small chemical groups, inside the carbon cage; such fullerenes are sometimes called endohedral fullerenes. Fullerenes may also be modified or derivatized to include chemical functional groups attached to the surface of the carbon cage.

SUMMARY

Described herein are methods for treating inflammatory disorders, comprising administering to a subject in need thereof a therapeutically effective amount of a synthetically modified fullerene.

In one embodiment, the inflammatory disorder is inflammatory arthritis.

In another embodiment, the inflammatory disorder is rheumatoid arthritis.

BRIEF DESCRIPTION OF THE DRAWINGS

FIG. 1 illustrates the attenuation of arthritis in fullerene-treated mice.

DETAILED DESCRIPTION

Figure 1A:
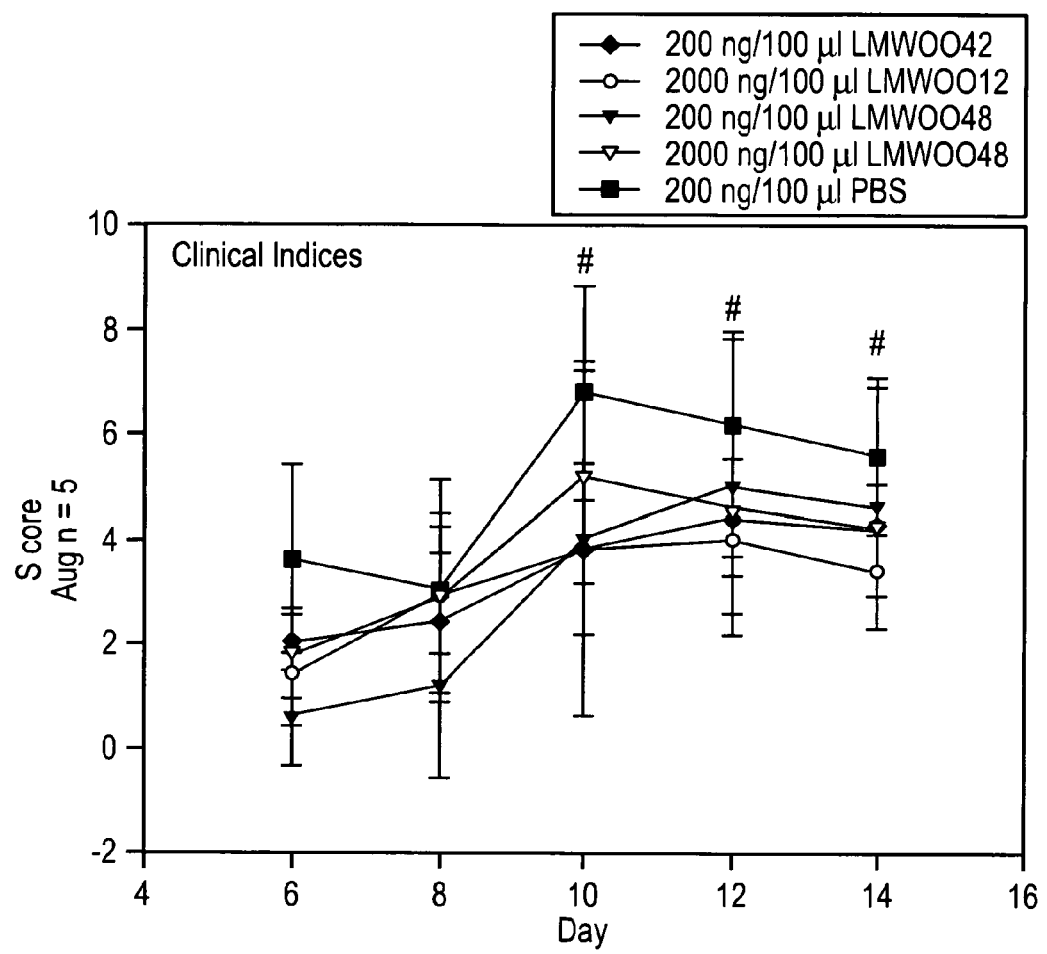
FIG. 1A shows clinical indices.

In accordance with this detailed description, the following definitions apply.

As used herein, the singular forms "a", "an", and "the" include plural referents unless the context clearly dictates otherwise. Thus, for example, reference to "compounds" includes a plurality of such compounds and reference to "the dosage" includes reference to one or more dosages and equivalents thereof known to those skilled in the art, and so forth.

The term "inflammatory disorder" or "inflammatory disease" is used to refer to abnormalities associated with inflammation, and comprises a large group of disorders. An inflammatory disorder can be associated with acute inflammation and/or chronic inflammation. Examples of inflammatory disorders include, without limitation, autoimmune diseases, inflammatory arthritis, rheumatoid arthritis, osteoarthritis, gouty arthritis, shoulder tendonitis or bursitis, polymyalgia rheumatica, inflammatory lung disease, asthma, type 1 diabetes melitis, multiple sclerosis, systemic lupus erthematosus, psoriasis, chronic prostatitis, glomerulonephritis, hypersensitivity reactions (such as type 2 and type 3 hypersensitivity), inflammatory bowel diseases (such as ulcerative colitis and Crohn's disease), pelvic inflammatory disease, reperfusion injury, transplant rejection, vasculitis, allergic reactions, inflammatory myopathies (such as dermatomyositis, polymyositis, and inclusion body myositis), and leukocyte defects (such as Chediak-Higashi syndrome and chronic granulomatous disease).

Inflammatory arthritis comprises a condition where arthritis is present because of localized joint inflammation. Rheumatoid arthritis, generally considered a type of inflammatory arthritis, involves many joints all of which are damaged to some degree by inflammation and it's sequelae. In certain embodiments, the inflammatory disorder described herein is an inflammatory arthritis, including but not limited to rheumatoid arthritis.

"Fullerene" or "fullerene molecule" as used herein refers to certain synthetically modified fullerene molecules as described herein, including amphiphilic or lipophilic synthetically modified fullerenes of the formula $Z_m-F-Y_n$; and hydrophilic or amphiphilic synthetically modified fullerenes of the formula $Z'_m-F-Y'_n$. The fullerenes comprise closed cages of 60 to 200 carbon atoms which may also include chemical moieties attached to the exterior and/or incorporated within the cage.

The amphiphilic or lipophilic synthetically modified fullerene molecules are described in copending U.S. patent application Ser. No. 2/073,230, U.S. Patent Application Publication No. 2008-0213324-A1, filed Mar. 3, 2008, entitled "AMPHIPHILIC OR LIPOPHILIC POLAR FUNCTIONALIZED FULLERENES AND THEIR USES," the entire disclosure of which is incorporated by reference herein.

The amphiphilic or lipophilic synthetically modified fullerene molecules as described in the copending application include fullerenes that have an aspect ratio≠1, with an equatorial band and two opposing poles, and comprise an adduct at one or both poles.

In one embodiment, the amphiphilic or lipophilic synthetically modified fullerene has the formula $Z_m-F-Y_n$;

wherein F is a fullerene of formula $C_p$ or $X@C_p$, the fullerene having two opposing poles and an equatorial region;

$C_p$ represents a fullerene cage having p carbon atoms, and $X@C_p$ represents such a fullerene cage having a chemical group X within the cage.

Z and Y are positioned near respective opposite poles of $C_p$;

m=1-5 and Z is a hydrophilic, lipophilic, or amphiphilic chemical moiety;

n=1-5 and Y is a lipophilic chemical moiety;

p=60-200 and p is an even number; and

X, if present, represents one or more metal atoms within the fullerene (F), optionally in the form of a trinitride of formula $G_{i=1-3}H_{k=3-i}N$ in which G and H are metal atoms.

In exemplary variations p is an even number between 60 and 120, with p=60-96 being more common and p=60 or p=70 being preferred. The synthetically modified fullerene can be arranged wherein each chemical moiety Z is composed of formula $A_rB$ in which A is a hydrophilic, lipophilic or amphiphilic chemical moiety, r=1-4, and B is a chemical linker connecting said A to the fullerene, and each chemical moiety Y is composed of formula $DE_v$ in which E is a lipophilic chemical moiety, v=1-4, and D is a chemical linker connecting the lipophilic chemical moiety to the fullerene.

The amphiphilic or lipophilic synthetically modified fullerene can be a prolate ellipsoid shaped fullerene having a major axis such that said poles are located at opposing ends of the major axis of the prolate ellipsoid fullerene. Alternatively, the fullerene can be spheroid with opposing poles defined by an axis through opposing carbon rings. Z and Y can configured such that when the molecule is contacted with a lipid bilayer in an aqueous medium, the equatorial region of F is selectively located within or in close proximity to the phospholipid bilayer. The molecule can be configured so that in an extended configuration has an aspect ratio of about 2.1 to 15, and a diameter less than about 2 nm. Such configurations are preferred configurations for incorporation of the molecules into lipid bilayers.

In another embodiment, the amphiphilic or lipophilic synthetically modified fullerene molecule has the formula $Z(C_p)Y$ wherein: p=60-200 carbons, preferably p=60 or 70; Y is a lipophilic moiety covalently connected to $C_p$, optionally through a linking group, at or near a pole thereof, and wherein Z is a lipophilic moiety, amphiphilic moiety, or a hydrophilic moiety covalently connected to $C_p$, optionally through a linking group, at or near a pole opposite to said Y; and, wherein said lipophilic moiety Y is capable of anchoring the synthetic fullerene molecule to a lipid membrane;

In another embodiment, the amphiphilic or lipophilic synthetically modified fullerene molecule has the formula $Z(C_p)Y$ wherein: p=60-200 carbons, preferably p=60 or 70; Y is a lipophilic moiety covalently connected to $C_p$, optionally through a linking group, at or near a pole thereof, and wherein Z is a hydrophilic moiety covalently connected to $C_p$, optionally through a linking group, at or near a pole opposite to said Y; and, wherein said lipophilic moiety Y is capable of anchoring the synthetic fullerene molecule to a lipid membrane.

In another embodiment, the amphiphilic or lipophilic synthetically modified fullerene molecule has the formula $Z(C_{70})Y$; wherein Y is a lipophilic moiety covalently connected to $C_{70}$, optionally through a linking group, at or near a pole thereof, and wherein Z is a lipophilic moiety, amphiphilic moiety, or a hydrophilic moiety covalently connected to $C_{70}$, optionally through a linking group, at or near a pole opposite to said Y; and, wherein said lipophilic moiety Y is capable of anchoring the synthetic fullerene molecule to a lipid membrane.

In another embodiment, the amphiphilic or lipophilic synthetically modified fullerene molecule has the formula $Z(C_{70})Y$ wherein: Y is a lipophilic moiety covalently connected to $C_p$, optionally through a linking group, at or near a pole thereof, and wherein Z is a hydrophilic moiety covalently connected to $C_p$, optionally through a linking group, at or near a pole opposite to said Y; and, wherein said lipophilic moiety Y is capable of anchoring the synthetic fullerene molecule to a lipid membrane.

In another embodiment the amphiphilic or lipophilic synthetically modified fullerene molecule can have the formula $Z_m-F-Y_n$ wherein:

F is a fullerene of formula $C_p$ having p=60-200 carbons, preferably p=60 or 70;

m=1-5 such that each Z is a group $ArBs$ in which r=1-4, s=1-4, and A is one or more hydrophilic or polar group bonded to the fullerene through one or more linker B;

n=1-5 and each Y is a group $D_tE_v$ in which t=1-4, v=1-4 and E is one or more lipophilic group bonded to the fullerene through one or more linker D; and, X and Y are positioned at or near opposite poles of F.

In certain embodiments the amphiphilic or lipophilic synthetically modified fullerene has a geometrical configuration capable of causing the fullerene molecule to locate within phospholipid bilayers of a cell such that a radical scavenging zone near the equatorial band of the fullerene is situated within or in close proximity to the phospholipid bilayer.

A plurality of such synthetically modified fullerene molecules can be uniformly dispersed in phospholipids, such as in liposomes. The amphipathic fullerene molecules described herein do not generally form vesicles by themselves, but require membrane-forming phospholipids in mole ratios greater than 1:1 (lipid:fullerene adduct) to form vesicles.

The methods described herein also encompass hydrophilic or amphiphilic synthetically modified fullerenes of the formula

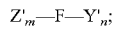

wherein F is a fullerene of formula $C_p$ or $X@C_p$, the fullerene having two opposing poles and an equatorial region;

$C_p$ represents a fullerene cage having p carbon atoms, and $X@C_p$ represents such a fullerene cage having a chemical group X within the cage;

Z' and Y' are positioned near respective opposite poles of $C_p$;

m=1-5 and Z' is a hydrophilic, lipophilic, or amphiphilic chemical moiety;

n=1-5 and Y' is a hydrophilic or amphiphilic chemical moiety;

p=60-200 and p is an even number; and

X, if present, represents one or more metal atoms within the fullerene (F), optionally in the form of a trinitride of formula $G_{i=1-3}H_{k=3-i}N$ in which G and H are metal atoms.

In exemplary variations p is an even number between 60 and 120, with p=60-96 being more common and p=60 or p=70 being preferred. The fullerene can be arranged wherein each chemical moiety Z' is composed of formula $A'_rB$ in which A' is a hydrophilic, lipophilic or amphiphilic chemical moiety, r=1-4, and B is a chemical linker connecting said A' to the fullerene, and each chemical moiety Y' is composed of formula $DE'_v$ in which E' is a hydrophilic or amphiphilic chemical moiety and, v=1-4, and D is a chemical linker connecting the chemical moiety Y' to the fullerene.

In another embodiment, the hydrophilic or amphiphilic synthetically modified fullerene molecule has the formula $Z'(C_p)Y'$ wherein: p=60-200 carbons, preferably p=60 or 70; Y' is a hydrophilic or amphiphilic moiety covalently connected to $C_p$, optionally through a linking group, at or near a pole thereof, and wherein Z' is a hydrophilic or amphiphilic moiety covalently connected to $C_p$, optionally through a linking group, at or near a pole opposite to said Y'.

In exemplary embodiments, Z' and Y' are both amphiphilic; Z' and Y' are both hydrophilic; or one of Z' and Y' is amphiphilic while the other is hydrophilic. In other embodiments, Z' is lipophilic and Y' is hydrophilic or amphiphilic.

In another embodiment, the hydrophilic or amphiphilic synthetically modified fullerene molecule has the formula $Z'(C_{70})Y'$; wherein Y' is a hydrophilic or amphiphilic moiety covalently connected to $C_{70}$, optionally through a linking group, at or near a pole thereof, and wherein Z' is a hydrophilic or amphiphilic moiety covalently connected to $C_{70}$, optionally through a linking group, at or near a pole opposite to said Y'.

Figure 3:
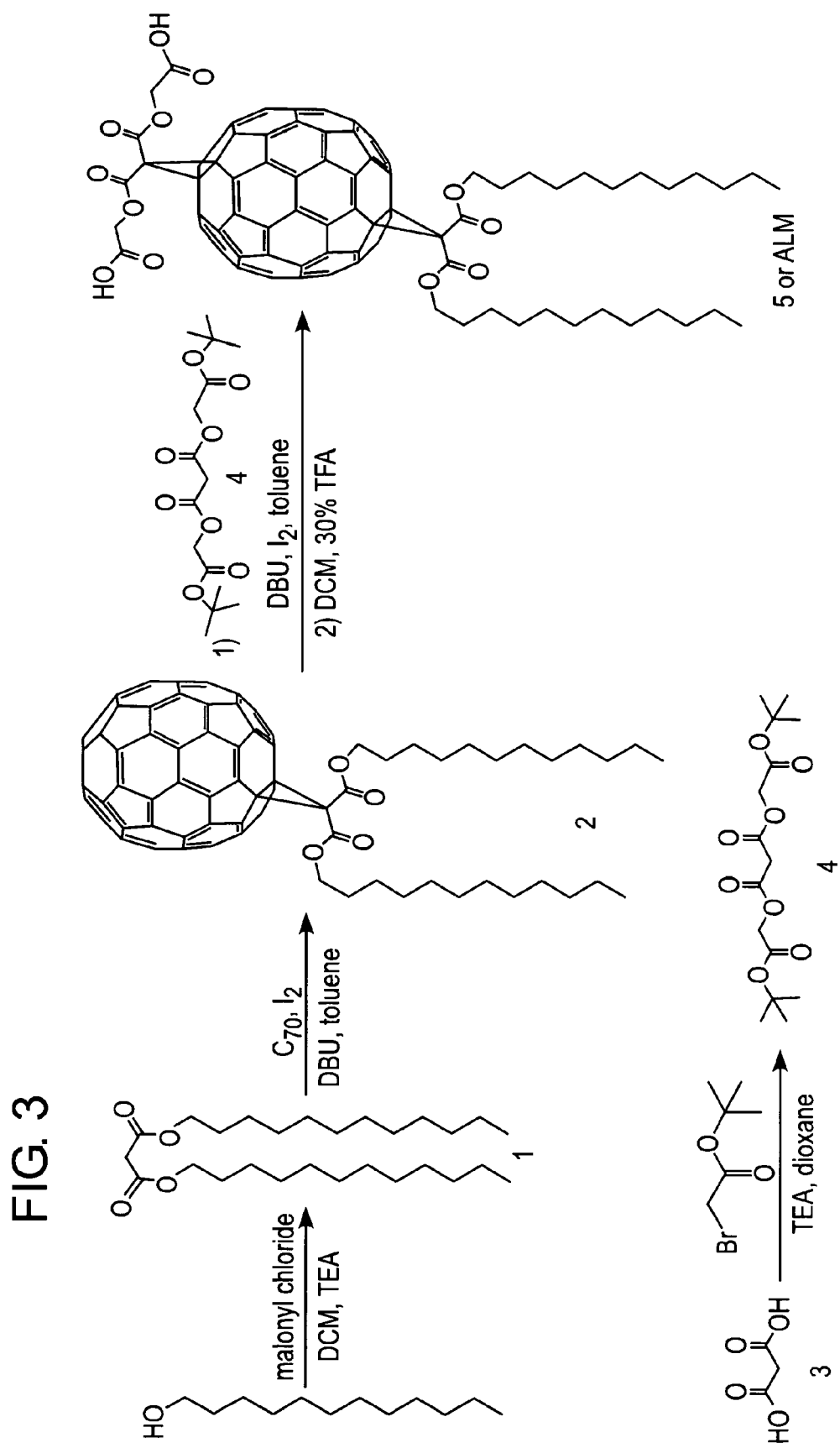
FIG. 3 illustrates an exemplary synthesis scheme for producing Compound 5.
Figure 4:
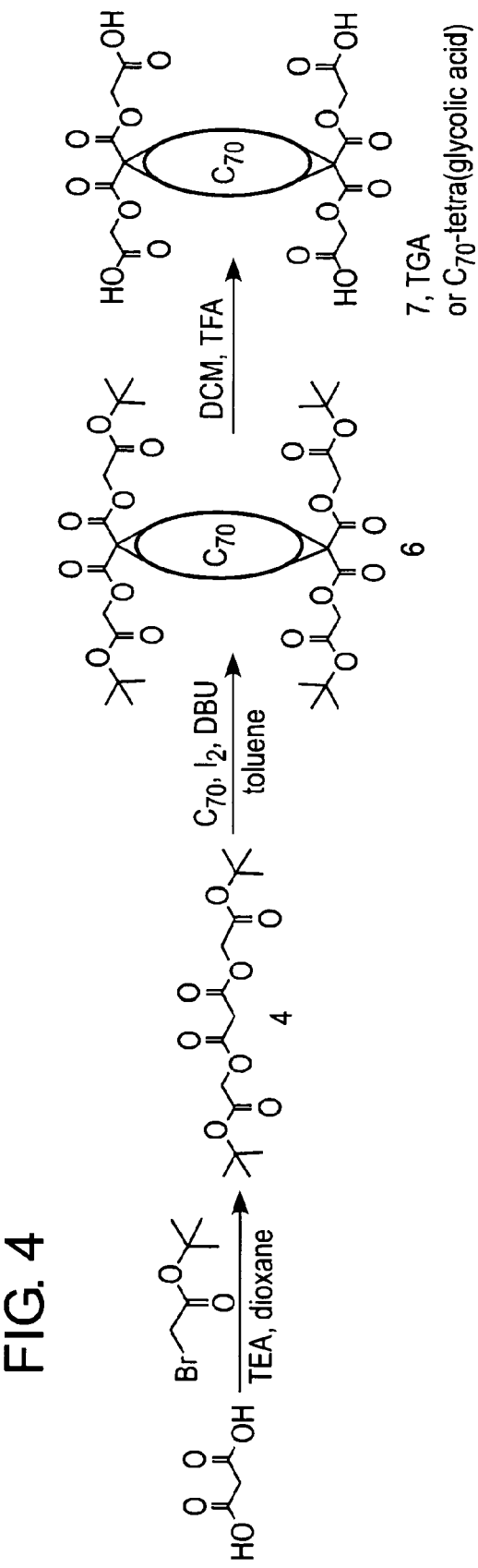
FIG. 4 illustrates an exemplary synthesis scheme for producing $C_{70}$-tetraglycolic acid, compound 7.
Figure 7:
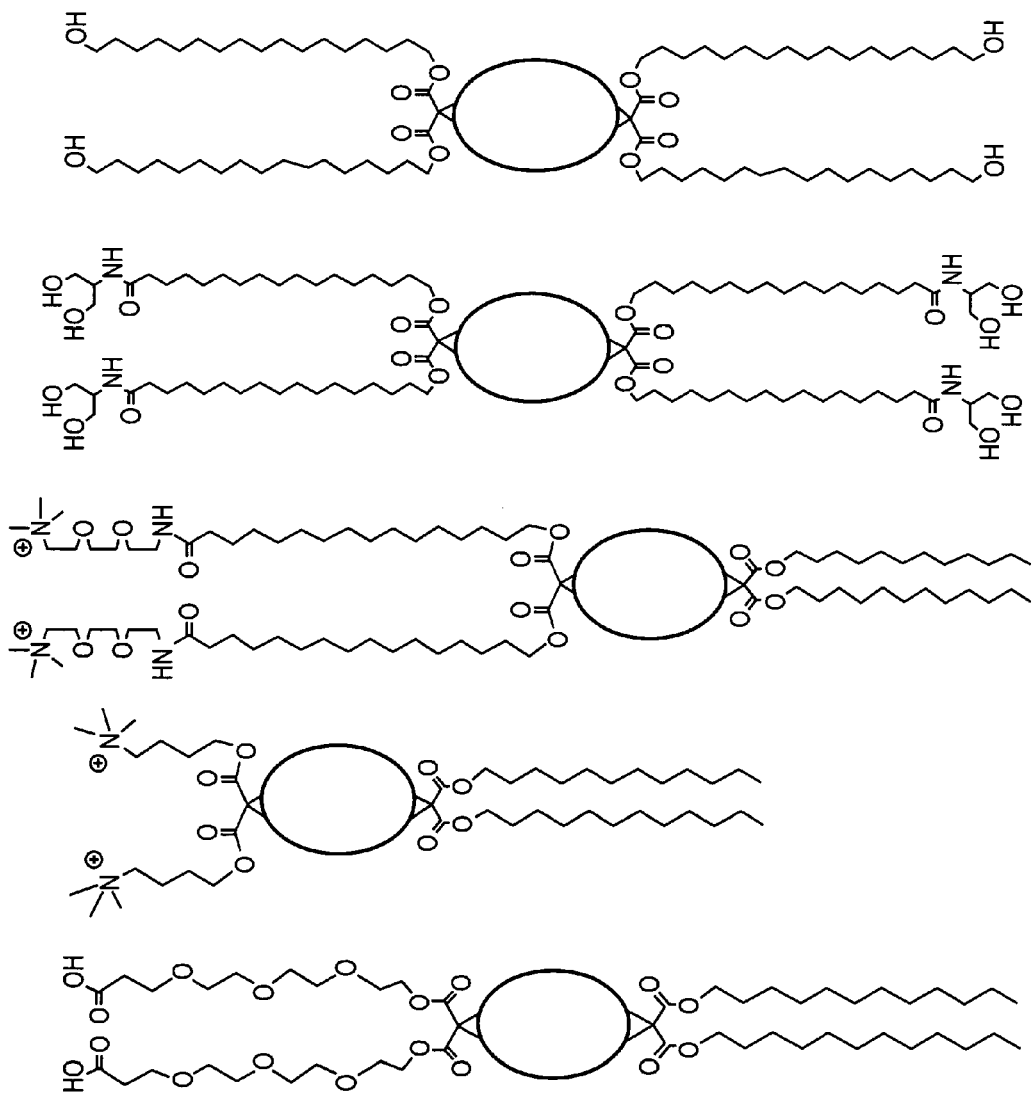
FIG. 7 illustrates additional non-limiting examples of synthetically modified fullerenes with any combination of hydrophilic, lipophilic, or amphiphilic chemical moieties.
Figure 8:
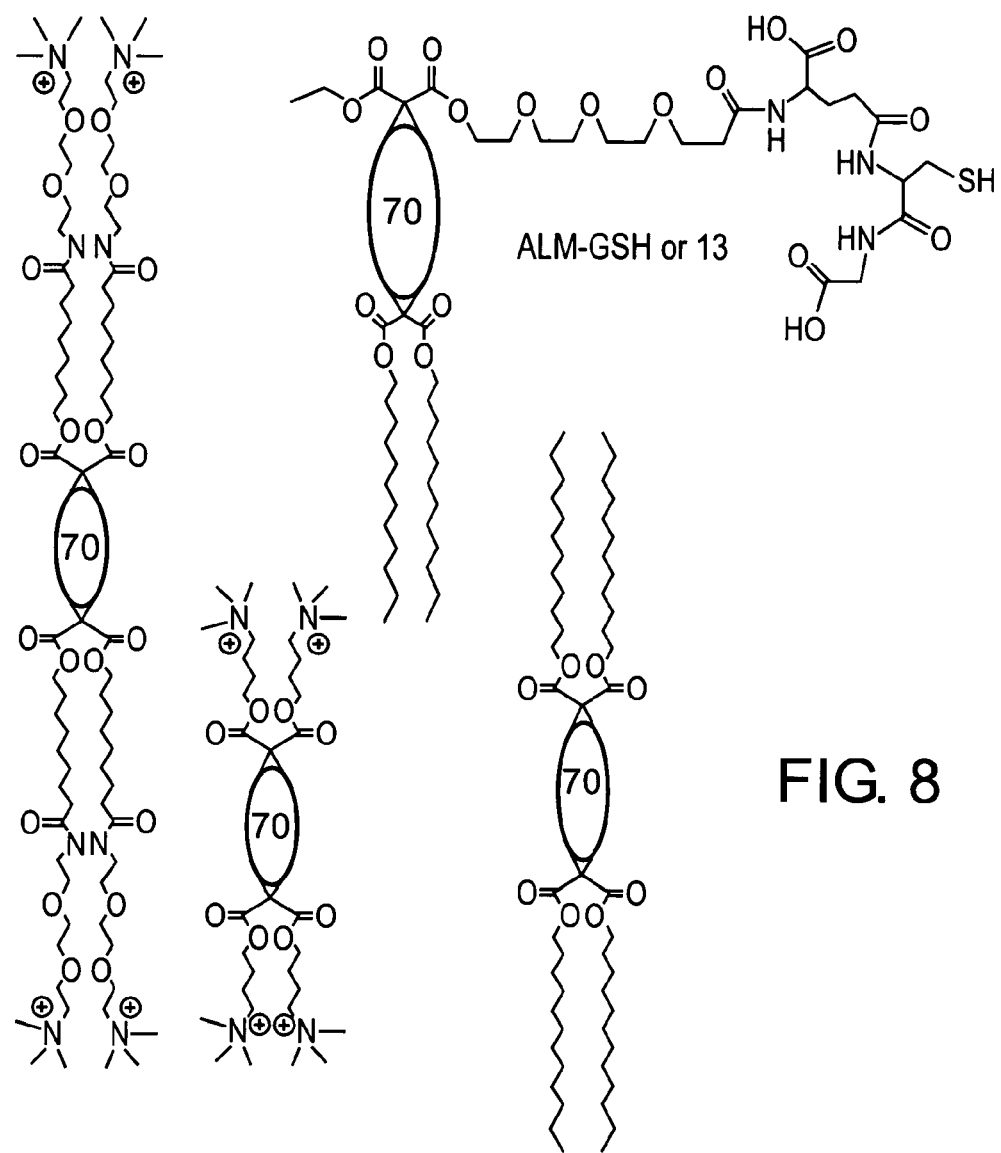
FIG. 8 illustrates additional non-limiting examples of synthetically modified fullerenes with any combination of hydrophilic, lipophilic, or amphiphilic chemical moieties.
Figure 9:
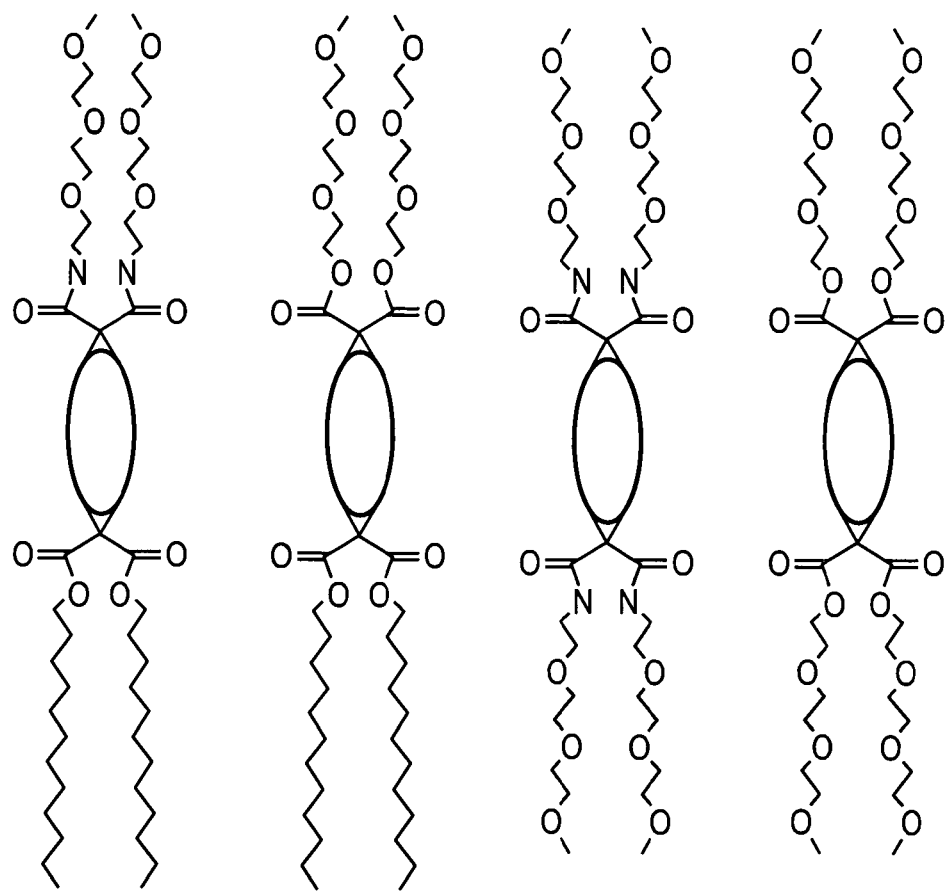
FIG. 9 illustrates additional non-limiting examples of synthetically modified fullerenes with any combination of hydrophilic, lipophilic, or amphiphilic chemical moieties.

In exemplary embodiments, the fullerene comprises any one or more of compounds 5, 13, 19, 7, 10, and 12, such as compound 5 (see FIG. 3) or compound 7 (see FIG. 4). In the present examples, compounds 5 and 7 comprise $C_{70}$. In other embodiments the fullerene comprises one or more of the additional compounds shown in the figures, for example FIGS. 7-9.

Suitable fullerencs are also described in the following patent applications and publications: U.S. application Ser. No. 12/921,106, filed on Sep. 3, 2010 and published as US 2011-0003773 A1, which is a national stage of PCT Application No. PCT/US2009/001334, filed on Mar. 3, 2009 and published as WO 2009/114089, entitled "USING FULLERENES TO ENHANCE AND STIMULATE HAIR GROWTH"; U.S. application Ser. No. 12/921,072, filed Sep. 3, 2010 and published as US 2011-0009486 A1, which is a national stage of PCT/US2009/001332, filed on Mar. 3, 2009 and published as WO 2009/114087, entitled "METHOD FOR TREATING PRURITUS BY ADMINISTERING FULLERENES"; U.S. application Ser. No. 12/921,083, filed on Dec. 16, 2010 and published as US 2011-0190251 A1, which is a national stage of PCT Application No. PCT/US09/01335, filed on Mar. 3, 2009 and published as WO 2009/114090, entitled "METHOD FOR INHIBITING THE BUILD-UP OF ARTERIAL PLAQUE"; U.S. application Ser. No. 12/921,143, filed on Sep. 3, 2010 and published as US 2011-0021630 A1, which is a national stage of PCT/US2009/001329, filed on Mar. 3, 2009 and published as WO 2009/114084, entitled "METHOD FOR TREATING WOUNDS BY ADMINISTERING FULLERENES"; the entire disclosures of which are incorporated by reference herein.

"Pharmaceutically acceptable salt" refers to pharmaceutically acceptable salts of fullerenes which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The terms "treating," "treatment," and the like are used herein to generally mean obtaining a desired pharmacological and physiological effect, and refer to complete elimination as well as to any clinically or quantitatively measurable reduction in the inflammatory condition for which the subject is being treated. "Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. More specifically, the fullerenes described herein which are used to treat a subject with an inflammatory disorder are provided in a therapeutically effective amount to prevent the disorder (i.e., inhibit the onset or occurrence of the disorder and/or cause the clinical symptoms of the disorder not to develop in a mammal that may be exposed to or predisposed to the disorder but does not yet experience or display symptoms of the disorder); inhibit the disorder (i.e., arrest or reduce the development of the disorder or its clinical symptoms); or relieve the disorder (i.e., cause regression of the disorder or its clinical symptoms). Subjects in need of treatment include those already with one or more inflammatory disorder as well as those in which one or more inflammatory disorder is to be prevented.

A "subject in need thereof" refers to any subject or individual who could benefit from the method of treatment described herein. In certain embodiments, a subject in need thereof is a subject predisposed for the development of one or more inflammatory disorders; a subject having one or more inflammatory disorders but not exhibiting any clinical symptoms; or a subject having one or more inflammatory disorders and suffering from the symptoms of the one or more iron inflammatory disorders. The "subject in need thereof" refers to a vertebrate, such as a mammal. Mammals include, but are not limited to, humans, other primates, rodents (i.e., mice, rats, and hamsters), farm animals, sport animals and pets. In one embodiment, the subject is a mammal such as a human. In certain embodiments, the methods find use in experimental animals, in veterinary application, and/or in the development of animal models for disease.

As used herein, the term "administering" or "introducing" a fullerene to a subject means providing the fullerene to a subject. Methods of administering fullerenes to subjects include any of a number of convenient means including, but not limited to, systemic administration (e.g. intravenous injection, intraparenteral injection, inhalation, transdermal delivery, oral delivery, nasal delivery, rectal delivery, etc.) and/or local administration (e.g. direct injection into a target tissue, delivery into a tissue via cannula, delivery into a target tissue by implantation of a time-release material, or delivery through the skin via a topical composition such as a cream, lotion, or the like), delivery into a tissue by a pump, etc., intraosseously, in the cerebrospinal fluid, or the like. "Orally delivery" refers to administration in an oral form, such as in a pharmaceutically acceptable carrier and/or diluent. Oral delivery includes ingestion of the drug as well as oral gavage of the drug. Further modes of administration include buccal, sublingual, vaginal, subcutaneous, intramuscular, or intradermal administration.

Modes of administration can include delivery via a sustained release and/or controlled release drug delivery formulation and/or device. "Sustained release" refers to release of a drug or an active metabolite thereof into the systemic circulation over a prolonged period of time relative to that achieved by oral administration of a conventional formulation of the drug. "Controlled release" is a zero order release; that is, the drug releases over time irrespective of concentration. Single, multiple, continuous or intermittent administration can be effected.

In one embodiment, a composition comprising fullerenes is administered orally to a subject having an inflammatory arthritis such as rheumatoid arthritis. In another embodiment, a composition comprising fullerenes is injected directly into an affected joint of a subject having an inflammatory arthritis such as rheumatoid arthritis. In yet another embodiment, a composition comprising fullerenes is administered via a topical formulation applied to the skin proximal to an affected joint of a subject having an inflammatory arthritis such as rheumatoid arthritis.

A "therapeutically effective amount" or "pharmaceutically effective amount" means the amount of a fullerene that, when administered to a subject for treating an inflammatory disorder, is sufficient to effect such treatment for the disorder. Thus a "therapeutically effective amount" is an amount indicated for treatment while not exceeding an amount which may cause significant adverse effects. The "therapeutically effective amount" will vary depending on the fullerene, and will also be determined by physical and physiological factors such the disorder and its severity, and the age, body weight, and/or clinical history of the subject to be treated. Methods for evaluating the effectiveness of therapeutic treatments are known to those of skill in the art.

Doses to be administered are variable according to the treatment period, frequency of administration, the host, and the nature and severity of the disorder. The dose can be determined by one of skill in the art without an undue amount of experimentation. The fullerenes are administered in dosage concentrations sufficient to ensure the release of a sufficient dosage unit into the patient to provide the desired treatment of the inflammatory disorder. The active ingredients may be administered to achieve therapeutic or prophylactic blood concentrations, such as in vivo plasma concentrations of the fullerenes of from about 0.01 to about 10,000 ng/cc, such as from about 0.01 to about 1,000 ng/cc. "Therapeutic or prophylactic blood concentrations" refers to systemic exposure to a sufficient concentration of a drug or an active metabolite thereof over a sufficient period of time to effect disease therapy or to prevent the onset or reduce the severity of a disease in the treated animal.

For example, the methods described herein may use compositions to provide from about 0.01 to about 100 mg/kg body weight/day of the fullerenes, from about 0.01 to about 10 mg/kg body weight/day of the fullerenes, or about 30 mg/kg body weight/day of the fullerenes. It will be understood, however, that dosage levels that deviate from the ranges provided may also be suitable in the treatment of a given disorder.

The fullerenes may be in any form suitable for administration. Such administrable forms include tablets, buffered tablets, pills, capsules, enteric-coated capsules, dragees, cachets, powders, granules, aerosols, liposomes, suppositories, creams, lotions, ointments, skin patches, parenterals, lozenges, oral liquids such as suspensions, solutions and emulsions (oil-in-water or water-in-oil), ophthalmic liquids and injectable liquids, or sustained- and/or controlled release forms thereof. The desired dose may be provided in several increments at regular intervals throughout the day, by continuous infusion, or by sustained and/or controlled release formulations, or may be presented as a bolus, electuary or paste.

"Practical dosage regimen" refers to a schedule of drug administration that is practical for a patient to comply with. For human patients, a practical dosage regimen for an orally administered drug is likely to be an aggregate dose of less than 10 g/day.

In one embodiment, a pharmaceutical composition or formulation comprising the fullerenes is prepared by admixture with one or more pharmaceutically acceptable carriers. Other products may be added, if desired, to maximize fullerene preservation, or to optimize a particular method of delivery. In addition, the present methods include use of combination compositions comprising the fullerenes as described herein in combination with other agents suitable for the treatment of inflammatory disorders.

"Pharmaceutically acceptable carrier" or "diluent" means a carrier that is useful in preparing a pharmaceutical composition that is generally safe, neither biologically nor otherwise undesirable, not toxic or otherwise unacceptable commensurate with a reasonable benefit/risk ratio, compatible with other ingredients of the formulation, and includes a carrier that is acceptable for veterinary use as well as human pharmaceutical use. "A pharmaceutically acceptable carrier" as used in the specification and claims includes both one and more than one such carrier.

A "pharmaceutically acceptable carrier" includes any and all solvents, dispersion media, coatings, antibacterial and anti-fungal agents, isotonic and absorption delaying agents, and the like, compatible with pharmaceutical administration of a composition comprising fullerenes. Examples of such carriers or diluents include, but are not limited to, water, saline, Ringer's solutions and dextrose solution. The volume of the pharmaceutical composition is based on the intended mode of administration and the safe volume for the individual patient, as determined by a medical professional.

The present disclosure relates to use of any one or more of the fullerenes described herein for the treatment of an inflammatory disease. The present disclosure also relates to the use of any one or more of the fullerenes described herein for manufacture of a medicament, particularly the manufacture of a medicament for treating inflammatory disease.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates, which may need to be independently confirmed. All publications, patents, patent applications and other references cited herein are hereby incorporated by reference.

While the disclosure has been described in detail with reference to certain embodiments thereof, it will be apparent to one skilled in the art that various changes can be made, and equivalents employed, without departing from the scope of the disclosure. In addition, the following examples are illustrative of the methods described herein and should not be considered as limiting the foregoing disclosure in any way.

EXAMPLES

Example 1

Figure 2:
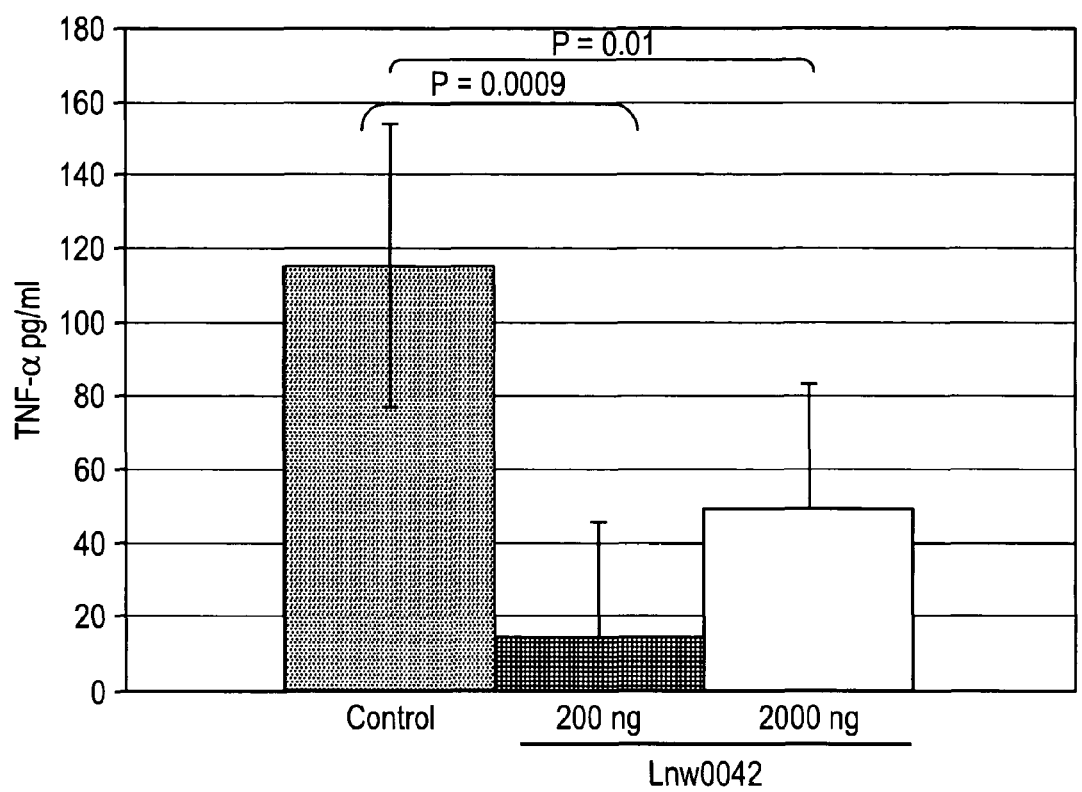
FIG. 2 illustrates the serum levels of TNF-α at day 14 in control and mice treated with fullerene derivatives.

Preparation of Amphiphilic Fullerene Derivative Depicted in FIG. 3 (Compound 5; Labeled LnW0042 in FIG. 2)

Step 1. Synthesis of Didodecylmalonate (Compound 1 in FIG. 3)
10 mmole dodecyl alcohol was dissolved in 30 mL dry dichloromethane (DCM), to which 12 mmole triethylamine (TEA) was added and stirred under nitrogen atmosphere. Then, 5 mmole malonyl chloride was dissolved in 1 ml dry DCM, and dropwise added to the above solution within a period of 10 minutes. Upon completion of the addition of malonyl chloride, the reaction mixture was stirred for a few hours and monitored by TLC. When reaction was completed, the reaction mixture was washed with brine twice and the combined organic phase was dried over MgSO4, filtered, and concentrated to 1-2 mL. Flash column with silica gel was used to purify the products with DCM as the solvents. Yield: 85%.

Step 2. Synthesis of $C_{70}$ Monoadduct (Compound 2 in FIG. 3)
840 mg (1.0 mmole) of $C_{70}$ was dissolved in 50 mL o-xylene and sonicated for 3 minutes, and then 400 mL toluene was added. Next, 1.0 mmole of the malonate 1 was added and the whole mixture was stirred, to which 1.0 mmole of iodine (MW=254 Da) was added. After stirred for 10 minutes, a 20 mL toluene solution of DBU (2.5 mmole, MW=151 Da, 1,8-diazabicyclo[5.4.0]undec-7-ene) was added to the mixture over a period of 15 minutes, and stirred for two hour. TLC monitored the reaction progress with 3:7 toluene/hexanes. Upon completion of the reaction, the product was concentrated to 10 mL (not to dryness) and 30 mL hexanes were added to dilute. Next, the mixture was loaded to the top of a silica gel column for purification. A mixture of solvents of 3:7 toluene/hexanes was used to elute unreacted $C_{70}$ (first band), and then the product (second band), which was then rotavaped and then pumped under vacuum for overnight before NMR and MALDI-MS. Yield: 60%.

Step 3. Synthesis of Compound 5
127.8 mg (0.1 mmole) of $C_{70}$ monoadduct 2 (MW=1278) was dissolved in 60 mL toluene. Next, 0.1 mmole of the malonate 4 (see detailed synthesis in Example 2) was added and the whole mixture was stirred, to which 0.1 mmole of iodine (MW=254 Da) was added. After stirred for 15 minutes, a 10 mL toluene solution of DBU (0.25 mmol, MW=151 Da) was added to the mixture over a period of 10 minutes, and stirred for two hour. TLC monitored the reaction progress with DCM or toluene/EA (98:2). When complete, the mixture was concentrated to 10 mL (not to dryness), and loaded to the top of a silica gel column for purification. Toluene was used first to elute unreacted $C_{70}$ monoadduct (first band), and then the product (second band), which was then rotavaped and then pumped under vacuum for overnight before NMR and MALDI-MS. Yield: 60%. The obtained the tert-butyl ester of ALM was dissolved in DCM and TFA (v:v 3:1) at 20 mg/mL and stirred at RT for 6 hours. Solvents were evaporated and dried under vacuum for overnight to quantitatively yield the final product ALM, which was characterized by MALDI-MS and NMR.

Example 2

Preparation of $C_{70}$-tetraglycolic Acid Depicted in FIG. 4 (TGA or Compound 7; Labeled "LnW0048" in FIG. 1)

Step 1. Synthesis of di(tert-butylacetoxy)malonate (Compound 4 in FIG. 4)
To a solution of malonic acid (40.0 mmol, 4.16 g) in dioxane was added 11.1 mL TEA (80.0 mmol). The mixture was stirred for 30 minutes, and then 11.8 mL (80.0 mmol) of tert-butyl bromoacetate in 12 mL dioxane was added and stirred over weekend. TLC monitored the reaction progress until completion. The precipitate was filtered and washed with ether. The filtrate was then washed with brine twice, dried over $MgSO_4$, and concentrated for NMR analysis. Yield: 75%.

Step 2. Synthesis of $C_{70}$ Tetraglycolic Acid Tert-butyl Ester (Compound 6 in FIG. 4)
840 mg (1.0 mmole) of $C_{70}$ was dissolved in 50 mL o-xylene and sonicated for 3 minutes, and then 200 mL toluene was added. Next, 2.0 mmole of the malonate 4 was added and the whole mixture was stirred, to which 2.0 mmole of iodine was added. After stirred for 10 minutes, a 20 mL toluene solution of DBU (5.0 mmole, MW=151 Da, 1,8-diazabicyclo[5.4.0] undec-7-ene) was added to the mixture over a period of 15 minutes, and stirred for 8 hours. TLC was used to monitor the reaction progress. When complete, it was concentrated to 40 mL and loaded onto the top of a silica gel column for purification. Toluene was used to remove unreacted $C_{70}$ and then DCM was to remove the monoadduct. Finally a mixture of EA and DCM was to elute the product, which was rotavaped and vacuum pumped for overnight for NMR and MALDI-MS. Yield: 70%.

Step 3. Synthesis of $C_{70}$ Tetraglycolic Acid (Compound 7)
The tert-butyl ester precursor 6 was dissolved in DCM at 20 mg/mL, and equal volume of TFA was added, and stirred overnight. TFA was removed by evaporation and water washing. The DCM layer was then dried to give pure TGA product. Yield: quantitative.

Example 3

Figure 5:
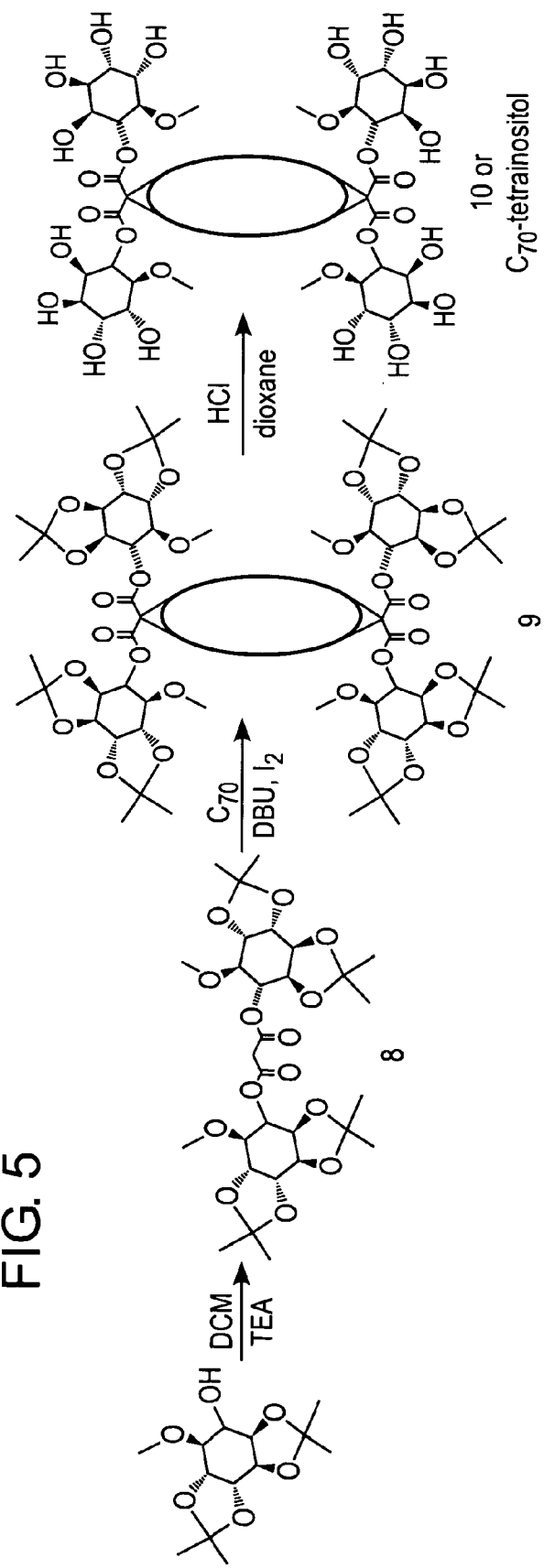
FIG. 5 illustrates an exemplary synthesis scheme for producing $C_{70}$-tetrainositol, compound 10.

Preparation of $7C_{70}$-Tetrainositol (Compound 10 in FIG. 5)

Step 1. Synthesis of Protected Inositol Malonate (Compound 8 in FIG. 5)
10 mmole 1,2; 5,6-bis-O-(1-methylethylene)-3-methyl-1D-chiro-inositol was dissolved in 50 mL dry DCM, to which 12 mmole TEA was added and stirred under nitrogen. Then, 5 mmole malonyl chloride was dissolved in 1 ml dry DCM, and dropwise added to the above solution within a period of 10 minutes. Upon completion of the addition, the reaction mixture was stirred for 6 hours. When completed, the reaction mixture was washed with brine twice and the combined organic phase was dried over $MgSO_4$, filtered, and concentrated to 1-2 mL. Flash column with silica gel was used to purify the products with 20% EA in DCM as the solvents. The product was colorless viscous liquid. Yield: 55%. Proton and carbon NMR confirmed the structure.

Step 2. Synthesis of $C_{70}$-tetrainositol-acetal Protected (Compound 9 in FIG. 5)

84 mg (0.1 mmole) of $C_{70}$ was dissolved in 60 mL toluene. Next, 0.2 mmole of the malonate 8 was added and the mixture was stirred, to which 0.2 mmole of iodine was added. After stirred for 15 minutes, a 10 mL toluene solution of DBU (0.50 mmol) was added to the mixture over a period of 10 minutes, and stirred for 6 hours. When it was complete, the reaction mixture was concentrated to 10 mL and loaded to the top of a silica gel column for purification. DCM was used first to elute unreacted $C_{70}$ and its monoadduct and then solvent was changed to DCM/EA to elute the product, which was rotavaped and pumped under vacuum for overnight before NMR and MALDI-MS.

Step 3. Synthesis of $C_{70}$-tetrainositol (Compound 10 in FIG. 5)

50 mg of the obtained octakis-acetal protected precursor compound 9 was dissolved in 20 mL 4.0 M hydrochloride solution in dioxane. A few drops of water was added and stirred for 30 hours. Complete deprotection was achieved. Solvent were removed completely and dried under vacuum overnight to yield pure final product, with NMR and MALDI-MS data confirmed.

Example 4

Figure 6:
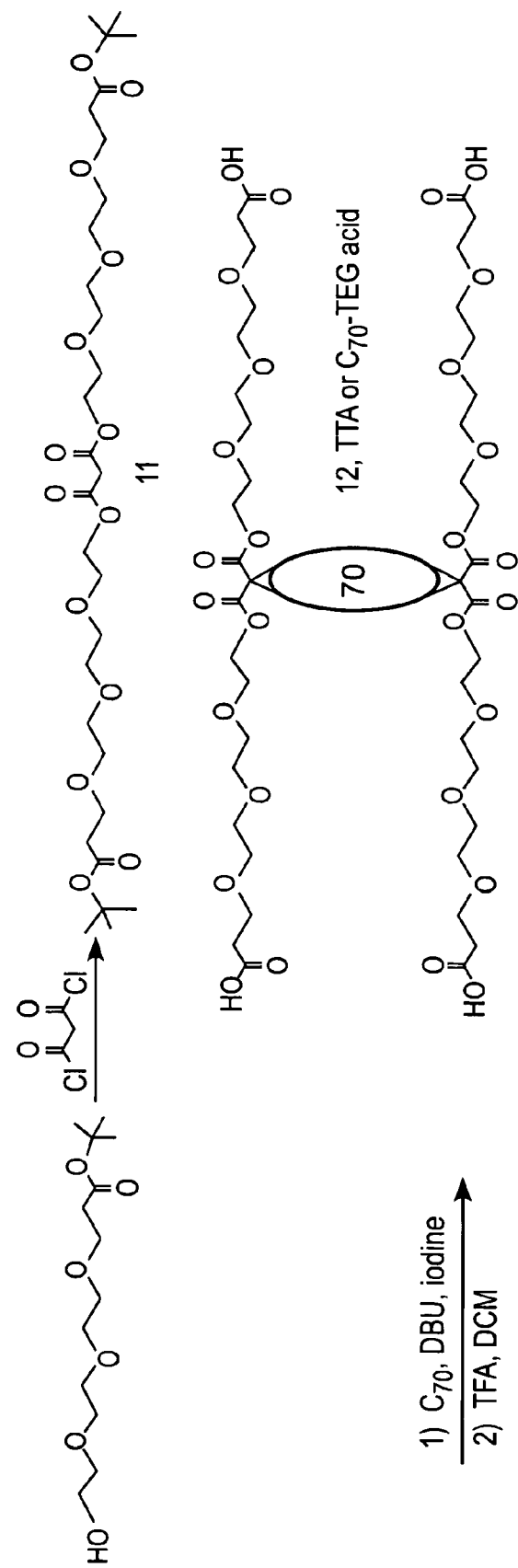
FIG. 6. Illustrates an exemplary synthesis scheme for producing $C_{70}$ TEG acid (TTA), compound 12.

Preparation of $C_{70}$-TEG Acid (Depicted in FIG. 6 as Compound 12 or TTA)

Step 1. Synthesis of di(tert-butyl TEG propionate) Malonate 11

10 mmole tert-butyl 12-hydroxy-4,7,10-trioxadodecanoate was dissolved in 50 mL dry DCM, to which 12 mmole TEA was added and stirred under nitrogen. Then, 5 mmole malonyl chloride was dissolved in 1 ml dry DCM, and dropwise added to the above solution within a period of 10 minutes. Upon completion of the addition, the reaction mixture was stirred for 4 hours. When completed, the reaction mixture was washed with brine twice and the combined organic phase was dried over $MgSO_4$, filtered, and concentrated to 1-2 mL. Flash column with silica gel was used to purify the products with DCM/EA as the solvents. Yield: 85%. Proton and carbon NMR confirmed the structure.

Step 2. Synthesis of $C_{70}$-TEG Acid 12

84 mg (0.1 mmole) of $C_{70}$ was dissolved in 60 mL toluene. Next, 0.2 mmole of the malonate 11 was added and the mixture was stirred, to which 0.2 mmole of iodine was added. After stirred for 15 minutes, a 10 mL toluene solution of DBU (0.50 mmol) was added to the mixture over a period of 10 minutes, and stirred for 6 hours. When it was complete, the reaction mixture was concentrated to 10 mL and loaded to the top of a silica gel column for purification. DCM was used first to elute unreacted $C_{70}$ and its monoadduct and then solvent was changed to DCM/EA to elute the product, which was rotavaped and pumped under vacuum for overnight before NMR and MALDI-MS. Yield: 70%. The obtained tert-butyl ester of $C_{70}$ TEG acid was dissolved in DCM and TFA (v:v 3:1) at 20 mg/mL and stirred at RT for 8 hours. Solvents were evaporated and dried under vacuum for overnight to quantitatively yield the final product $C_{70}$ TEG acid, which was characterized by MALDI-MS and NMR.

Example 5

Figure 10:
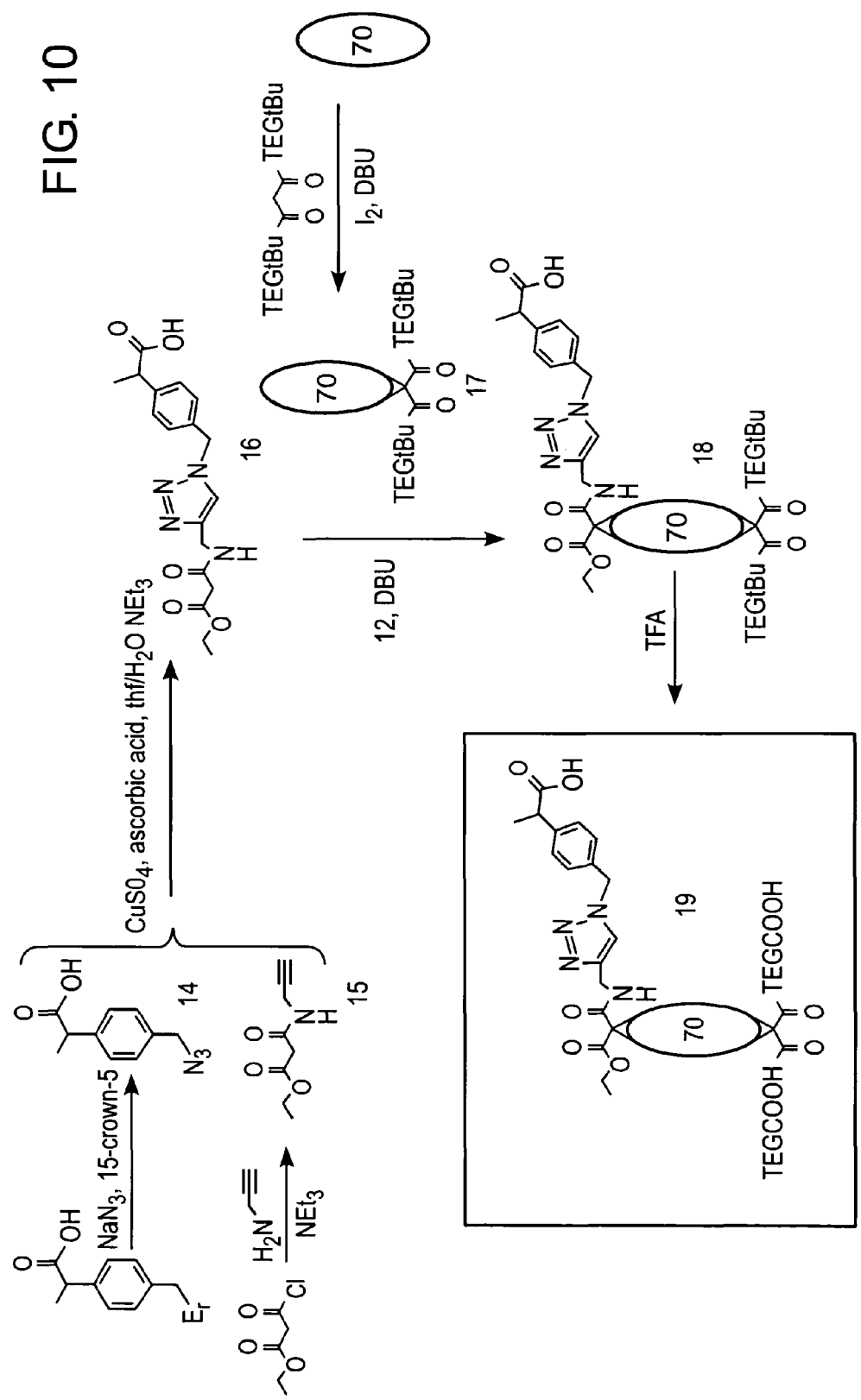
FIG. 10 illustrates an exemplary synthesis scheme for producing $C_{70}$ with a phenyl propionic acid group as one of its hydrophilic groups.

Preparation of Phenylpropionic Acid-triazole-mixed Malonateamide-$C_{70}$-TEG-COOH (Compound 19 (FIG. 10))

Step 1. Synthesis of 2-(4-azidomethylphenyl)-propionic Acid (Compound 14 in FIG. 10)

To a solution of 2-(4-bromomethylphenyl)-proprionic acid (1.5 g) in 1,4-dioxane was added $NaN_3$ (5 g) and 15-crown-5 (100 mg). The mixture was heated to 80° C. for 16 h, then cooled. The solvent was removed under reduced pressure, and the residue chromatographed on silica to yield 2-(4-azidomethylphenyl)-proprionic acid as an off white solid.

Step 2. Preparaton of Acetylene Malonate (Compound 15)

To a separate solution of ethoxy malonyl chloride was added triethylamine and propargyl amine in equal molar equivalents. The mixture was stirred 20 minutes and purified by column chromatography.

Step 3. Preparation of Triazole Propionic Acid (Compound 16)

A mixture of the acetylene malonate (1 equivalent), 2-(4-azidomethylphenyl)-propionic acid (1 equivalent), $CuSO_4$ (5 mol %), triethylamine (5 equivalents), and ascorbic acid (50 mol %) was stirred in 1:1 THF:water overnight following a procedure widely used in the literature. Solvents were removed under reduced pressure and the residue was extracted with ethyl acetate and water. The ethyl acetate layer was further purified by column chromatography to yield the triazole product.

Step 4. Preparation of Bis(Tert-butyl Hydroxy Trioxadodecanoate (Compound 17)

bis(tert-Butyl 12-hydroxy-4,7,10-trioxadodecanoate)malonate was synthesized by reaction with 12, DBU, and $C_{70}$ in xylene, followed by column chromotography purification.

Step 5. Preparation of Triazole Propionic Acid Malonamide (Compound 18)

Using the $C_{70}$ mono-adduct from above, $I_2$, DBU, and the triazole-containing malonamide, a second adduct were added to the $C_{70}$ cage. After 20 minutes of reaction under nitrogen at room temperature, the reaction was poured onto a silica column and purified by chromatography.

Step 6. Synthesis of Compound 19

Finally, deprotection of the t-butyl esters was achieved by reaction with trifluoroacetic acid in CH2C12 (1:1) overnight. Volatiles were removed under reduced pressure to yield the product, 19.

Example 6

Fullerene Derivatives in a Murine Arthritis Model

Figure 1B:
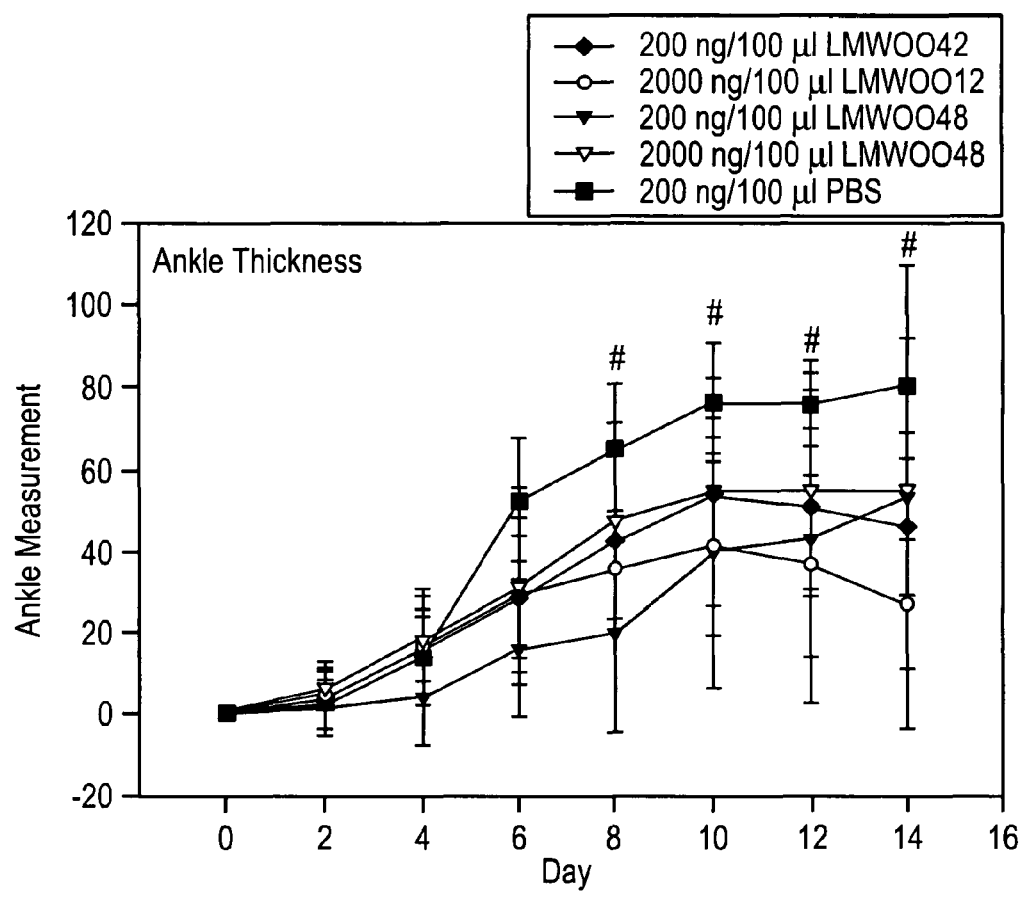
FIG. 1B shows ankle thickness.

To induce disease, C57/B6 (5 mice/cage/group) mice were injected intraperitoneally (IP) on Days 1 and 3 with 100 μl of arthritogenic serum. Fullerene derivatives (200-2000 ng/100 μl phosphate buffered saline (PBS)) were injected IP on Day 0, 2, and every 2nd day thereafter. As a control 100 μl of PBS without serum was injected in the control group. Swelling in each ankle was measured along with the clinical indices as described (Lee, D M, Science. 2002 Sep. 6; 297(5587):1689-92). Measurements were performed every second day by personnel blinded to the identity of the injections. After 14 days mice were sacrificed and ankle sections removed for histology and serum obtained for cytokine analysis. Error bars, SEM. In FIG. 1A clinical index was given as the sum of observed inflammation (per paw): 0=no evidence of inflammation; 1=subtle inflammation (metatarsal phalanges joints, individual phalanx, or localized edema); 2=easily identified swelling but localized to either dorsal or ventral surface of paw; and 3=swelling on all aspects of paw. Maximum score=12. In FIG. 1B the sum of the measurement in ankle swelling at each day was given. The * indicates significant differences observed on that day in fullerene compared to non-fullerene-treated mice.

Tumor necrosis factor-alpha (TNF-α) is a major mediator of inflammatory arthritis. Several clinical trials have shown that TNF-α blocking agents, such as etanercept (co-marketed by Amgen and Wyeth under the trade name ENBREL®); infliximab (marketed under the trade name REMICADE® by Centocor); and adalimumab (marketed as HUMIRA® by Abbott Laboratories, Illinois, U.S.A.), significantly reduce the morbidity associated with inflammatory arthritis. As seen in FIG. 2, TNF-α in the serum at day 14 was significantly inhibited in the mice treated with fullerene derivatives. These results demonstrate that fullerene derivatives can inhibit inflammatory arthritis, possibly through the inhibition of TNF-α.

Prior to injection, 5 was incorporated into liposomes with egg phosphatidylcholine (PC) at a ratio of 1:2.7 was dissolved in PBS buffer at pH 7.4.

In FIG. 1, LNW0042 refers to compound 5 (see, e.g., FIG. 3), and LNW0048 refers to compound 7 (see, e.g., FIG. 4).

The mouse arthritis model is characterized by the development of disease with many of the features of rheumatoid arthritis in humans. As seen in FIGS. 1 and 2, different fullerene formulations inhibited inflammatory arthritis. After arthritogenic serum transfer, PBS-treated mice exhibited typical clinical arthritis as determined using clinical indices and quantitative ankle swelling measurements. In contrast, mice treated with fullerene derivatives demonstrated a significant inhibition in both the clinical indices as well as ankle swelling measurements. Inflammation was significantly inhibited (p<0.04) by 5 from day 6 to 14. At day 14, concentrations of 200 ng/100 ul or 2000 ng/100 μl both had p<0.0001. In addition, at 200 ng/100 μl 7, inflammation was significantly inhibited from days 6 to 12 (p<0.03) and 2000 ng/100 μl inflammation was significantly inhibited from days 10 to 14 (p<0.02)

Example 7

TNF-α Inhibition in Cultured Mast Cells

Mast Cells (MC) are a component of the inflammatory response. As such, cultures of human Mast Cells can be used for screening the activity of different fullerene derivatives to evaluate their potential activity in animal models. In this example, Mast Cells extracted from human skin were cultured. Cultures were maintained for up to two months in X-VIVO 15™ media with stem cell factor and were 100% skin Mast Cells ("SMC").

SMC were suspended in fresh medium (without cytokines) and incubated overnight with or without fullerenes 5 (ALM), 7 (TGA), 10 (tetrainositol), 12 (TTA) and 19 (propionic acid) at 37° C. in a 6% $CO_2$ incubator. The next morning, cells were stimulated with FcεRI Abs (1 μg/ml) for 30 minutes (β-hexosaminidase) or overnight (cytokines GM-CSF and TNF-α) at 37° C. in a 6% $CO_2$ incubator. The percent β-hexosaminidase release was determined by dividing the amount of β-hexosaminidase in the supernatant by the total amount detected in the supernatant and cell pellet. TNF-α or GM-CSF secretion was measured by standard ELISA. In some experiments lysates from cells were prepared for Western blotting with various antibodies.

To assess the in vitro effects of fullerenes on Mast Cell cytokine production, cells were incubated for 16 hours with fullerene derivatives and then stimulated overnight with α-FcεRI Abs. The untreated MC secreted nearly 900 pg/ml and 200 pg/ml of GM-CSF and TNF-α cytokine, respectively. The fullerene derivatives depicted in FIG. 3 (5), FIG. 4 (7 or "TGA"), FIG. 5 (10) FIG. 6 (12) FIG. 8 (13) and FIG. 10 (19) inhibited TNF-α secretion significantly. Of these 7 and 10 reduced GM-CSF secretion 60% or greater. TNF-α release was not reduced as significantly, however, compounds 7, and 10 reduced the detectable amounts between 30% and 40%. An unexpected result from these experiments showed that the tetrainositol derivative 10 did not inhibit Mast Cell degranulation, yet was potent at blocking cytokine release.

The invention claimed is:

1. A compound selected from the group consisting of $C_{70}$-tetraglycolic acid, $C_{70}$-tetrainositol, $C_{70}$-TEG acid, and phenylpropionic acid-triazole-mixed malonateamide-$C_{70}$-TEG-COOH.

2. A method for treating an inflammatory disease, comprising administering to a subject in need thereof a therapeutically effective amount of a compound according to claim 1.

3. A composition comprising a compound according to claim 1.

* * * * *